(12) United States Patent
Jez et al.

(10) Patent No.: US 7,837,833 B2
(45) Date of Patent: Nov. 23, 2010

(54) METHOD FOR CHARACTERIZING FIBROUS MATERIALS USING STOKES PARAMETERS

(75) Inventors: David R. Jez, Vancouver (CA); Frank M. Haran, Vancouver (CA); Graham I. Duck, Vancouver (CA)

(73) Assignee: Honeywell ASCA Inc., Mississauga, ON (CA)

( * ) Notice: Subject to any disclaimer, the term of this patent is extended or adjusted under 35 U.S.C. 154(b) by 510 days.

(21) Appl. No.: 11/877,128

(22) Filed: Oct. 23, 2007

(65) Prior Publication Data

US 2009/0101297 A1  Apr. 23, 2009

(51) Int. Cl.
*D21F 11/00* (2006.01)
*G01N 21/84* (2006.01)

(52) U.S. Cl. ............... 162/198; 356/35; 356/429

(58) Field of Classification Search ............. 162/198; 356/35, 429
See application file for complete search history.

(56) References Cited

U.S. PATENT DOCUMENTS

| | | | |
|---|---|---|---|
| 4,955,720 | A | 9/1990 | Blecha et al. |
| 5,394,247 | A | 2/1995 | Vahey et al. |
| 5,640,244 | A | 6/1997 | Hellstrom et al. |
| 5,812,404 | A | 9/1998 | Hamalainen et al. |
| 5,825,653 | A | 10/1998 | Huovila et al. |
| 6,300,954 | B1 | 10/2001 | Sato et al. |
| 6,961,123 | B1 | 11/2005 | Wang et al. |
| 2003/0156293 | A1 | 8/2003 | Kazuhiko et al. |
| 2006/0237156 | A1 | 10/2006 | Shakespeare et al. |
| 2008/0291463 | A1* | 11/2008 | Milner et al. ........ 356/491 |

FOREIGN PATENT DOCUMENTS

WO  WO 2006/118619 A1  11/2006
WO  WO 2007/082371 A1 *  7/2007

OTHER PUBLICATIONS

Hewlett-Packard Company, The Poincare Sphere, 1995, Hewlett-Packard Journal, p. 29.*
Tourlonias et al., Polarimetric measurements for fabric surface state characterization, 2006, SPIE 6189, pp. 61890N.*
Tourlonias et al., Characterization of thermobonded nonwovens by polarizing imaging, 2007, SPIE 6682, pp. 66820Q.*
Toulonias et al., Polarimetric measuements of fabric surfaces, Aug. 2007, Optical Engineering, 46(8).*
L. Giudicotti, M. Brombin, "Data analysis for a rotating quarter-wave, far-infrared Stokes polarimeter", Applied Optics, pp. 2638-2648, vol. 46, No. 14, May 2007.
M. Reid, R. Fedosejevs, "Terahertz birefringence and attenuation properties of wood and paper", Applied Optics, pp. 2766-2772, vol. 45, No. 12, Apr. 2006.

* cited by examiner

*Primary Examiner*—Matthew J. Daniels
*Assistant Examiner*—Anthony J Calandra
(74) *Attorney, Agent, or Firm*—Jetter & Associates, P.A.

(57) ABSTRACT

An apparatus (200) for determining fiber orientation parameters of a sheet of material during a production process includes a polarized radiation generating system (201, 202) operable for providing polarized radiation having a frequency of at least $1 \times 10^8$ Hz. The radiation is aligned to be incident on a sheet of material to be characterized (203). A polarimeter (204, 205) is aligned to receive the radiation transmitted by the sheet of material (203). A photodetector (206) is provided for measuring radiation received after polarization processing by the polarimeter. A processor (207) is coupled to the photodetector (206) for calculating Stokes parameters of the moving sheet (203) based upon intensities of the radiation received and determines at least one parameter relating to fiber orientation of the moving sheet based upon the Stokes parameters.

11 Claims, 4 Drawing Sheets

METHOD FOR CHARACTERIZING FIBROUS MATERIALS USING STOKES PARAMETERS

FIELD OF THE INVENTION

The present invention relates to methods and apparatus for measurement of fiber orientation, and more particularly Stokes parameters based methods and apparatus suitable for measurement of fiber orientation in a moving sheet.

BACKGROUND

The fiber orientation of fibrous materials is known to often dictate certain properties of the material. The orientation of the cellulose fibers in paper products is an important property to monitor and control during its manufacture.

Fiber orientation is the term used to describe how fibers lay within a sheet of paper. Identifying the direction the majority of fibers are aligned in (Fiber Orientation Angle), and the degree of alignment (Fiber Ratio or Aspect Ratio), characterizes the fiber orientation. The fiber orientation angle is typically a measurement of the angle between the machine direction (MD) motion of the sheet and the principal direction of fiber orientation. The Fiber Ratio is a measurement of the sheet anisotropy (exhibiting properties with different values when measured in different directions) and is the ratio of maximum to minimum fiber distribution 90 degrees apart. An isotropic sheet will have a fiber ratio of one. The Aspect Ratio describes the relative fiber numbers oriented with the fiber orientation angle and perpendicular to the fiber orientation angle.

The fiber orientation of paper is known to dictate important properties such as strength and warp (twist/curl). Strength is particularly important for board (strong boxes) and sack grade (strong bags). Warp is important for box manufacturers where it is desired for the box to be square and for photocopy paper to prevent paper jams. Strength is also important in the printing process since it is generally desired to "pull" the paper through the printing presses as fast as possible. For these reasons paper manufacturers want to optimize fiber orientation in order to maximize strength and minimize warp. Fiber orientation measurement is preferably performed during paper production so that processing conditions can be changed to provide the desired optimum orientation. However, fiber orientation measurements can also be used as a quality control step to determine fiber orientation of the paper obtained as finished product.

Various apparatus for this purpose are known. One method uses a fiber orientation measuring apparatus adapted to detect a differential magnitude of two extreme values of fiber orientation, using a diffusion effect (i.e., light guide effect). This fiber orientation measuring apparatus of well known art detects any extreme fiber orientation appearing in roll paper, particularly running roll paper and/or detects a differential magnitude of two such extreme fiber orientations. In this case, the paper web is irradiated with electromagnetic radiation having a sharp boundary over at least 180 degrees in its cross-section, particularly the laser beam of visible spectrum (visible light). Then, in the vicinity of incident spot on the incident side of the paper web or on the side opposed thereto, the beam transmitted through the paper web is divided into a plurality of predetermined sectors, measured at the position at a predetermined distance from the boundary between the incidence spot and non-incidence region and the measured values in the form of electrical values are compared to each other. To obtain such electrical values, the light beam transmitted through the paper web is optically magnified and guided through an image pick-up lens to obtain an image which is then subjected to photoelectric conversion.

The well known method and apparatus to measure the paper fiber orientation as described above is based on a principle such that a detector is rotated around the optical axis of the incident laser beam to divide this into a plurality of predetermined shapes over the given angle and thereby to obtain a difference or a ratio between the maximum value and the minimum value. However, such method and apparatus have been accompanied with various problems as follow. First, it may be impossible to detect the maximum value and the minimum value at one and same position on the paper web being made since the web is running during rotation of the detector. In order that such apparatus of well known art can achieve the desired measurement, it is essential that the paper fiber orientation to be determined should be constant at any position on the paper web. Regrettably, the fiber orientation more or less depends on the particular position on the paper web being made and therefore it may be impossible for this apparatus of well known art to detect the fiber orientation being variable as the paper web runs. Thus, it may be substantially impossible to, on-line, determine the fiber orientation of the web running through the paper making machine. In other words, it may be impossible to reflect the result of measurement instantaneously in paper being made and thereby to obtain paper having desired fiber orientation.

Additionally, the paper web may be affected by variable running velocity as well as variable diameter of wind-up roll and may shake and/or vibrate in a direction substantially perpendicular to its surface. Consequently, it is difficult to maintain the distance between the paper web and the image pick-up lens constant and thereby to maintain the image in well focused condition. Distinctness as well as shape of the image in the imaging plane may vary due to shaking and/or vibration of the web. Such variation may not be related to an actual variation in the fiber orientation and the intensity of the light beam determined by the detector at a predetermined position for measurement may vary independently of the actual fiber orientation.

In view of the problems as have been described above, it is an object of the present invention to provide method and apparatus to measure fiber orientation of fibrous materials including paper so that the fiber orientation in the fibrous materials such as a paper web being run can be measured on-line reliably. Once provided, the result of measurement can be instantaneously reflected on the paper being made in order to obtain paper of consistently high quality.

SUMMARY

The Summary is provided to comply with 37 C.F.R. §1.73, requiring a summary of the invention briefly indicating the nature and substance of the invention. It is submitted with the understanding that it will not be used to interpret or limit the scope or meaning of the claims.

A method for determining fiber orientation parameters of a sheet of material during a production process comprises the steps of irradiating a sheet of material to be characterized with polarized radiation having a frequency of at least $1 \times 10^8$ Hz, measuring radiation intensities transmitted by the sheet of material, calculating Stokes parameters for the sheet based upon the measured radiation intensities, and determining at least one fiber orientation parameter from the Stokes parameters. In one embodiment the sheet material is a moving sheet of material, such as cellulose comprising fiber material, for example, paper being manufactured.

In one embodiment the polarized radiation is generated from an unpolarized terahertz or microwave source using a polarizer, or provided directly from a polarized terahertz or microwave source. The determining step can comprise displaying the Stokes parameters on a Poincare sphere, and determining birefringence of the sheet and the fiber orientation parameter using the Poincare sphere.

The method can further comprise the step of automatically modifying at least one parameter of the production process based on the Stokes parameters or the fiber orientation parameter. In one embodiment the parameter of the production process comprises at least one of jet to wire ratio (Rush/Drag) and slice lip opening.

A polarimeter comprising a rotating quarter wave plate optically coupled to a linear polarizer can be used for the measuring step. In one embodiment the method further comprises the step of determining an input polarization state of the polarized radiation in an absence of the sheet of material, and using the input polarization state in the calculating stop. In another embodiment the angle between the sheet of material and the polarized radiation is held constant during the method.

An apparatus for determining fiber orientation parameters of a sheet of material during a production process comprises a polarized radiation generating system operable for providing polarized terahertz or microwave radiation having a frequency of at least $1\times10^8$ Hz. The polarized radiation is aligned to be incident on a sheet of material to be characterized. A polarimeter is aligned to receive the radiation transmitted by the sheet of material. A photodetector is provided for measuring radiation received after polarization processing by the polarimeter. A processor is coupled to the photodetector for calculating Stokes parameters of the moving sheet based upon intensities of the radiation received and determining at least one parameter relating to fiber orientation of the moving sheet based upon the Stokes parameters.

In one embodiment the sheet of material is processed by a processing system, further comprising closed loop control between the processor and the processing system for automatically modifying at least one parameter of a process run by the production system based on the Stokes parameters or the fiber orientation parameter. The closed loop control can comprise a wired feedback connection or an over-the-air connection comprising a transmitter and an antenna coupled to the processor and a receiver coupled to the processing system.

The production process parameter can comprise at least one of jet to wire ratio (Rush/Drag) and slice lip opening. In one embodiment the polarized radiation generating system comprises an unpolarized radiation source coupled to a first linear polarizer. The unpolarized radiation source can comprises a terahertz source.

The above-described and other features and advantages of the present disclosure will be appreciated and understood by those skilled in the art from the following detailed description, drawings, and appended claims.

DETAILED DESCRIPTION OF THE INVENTION

Figure 1:
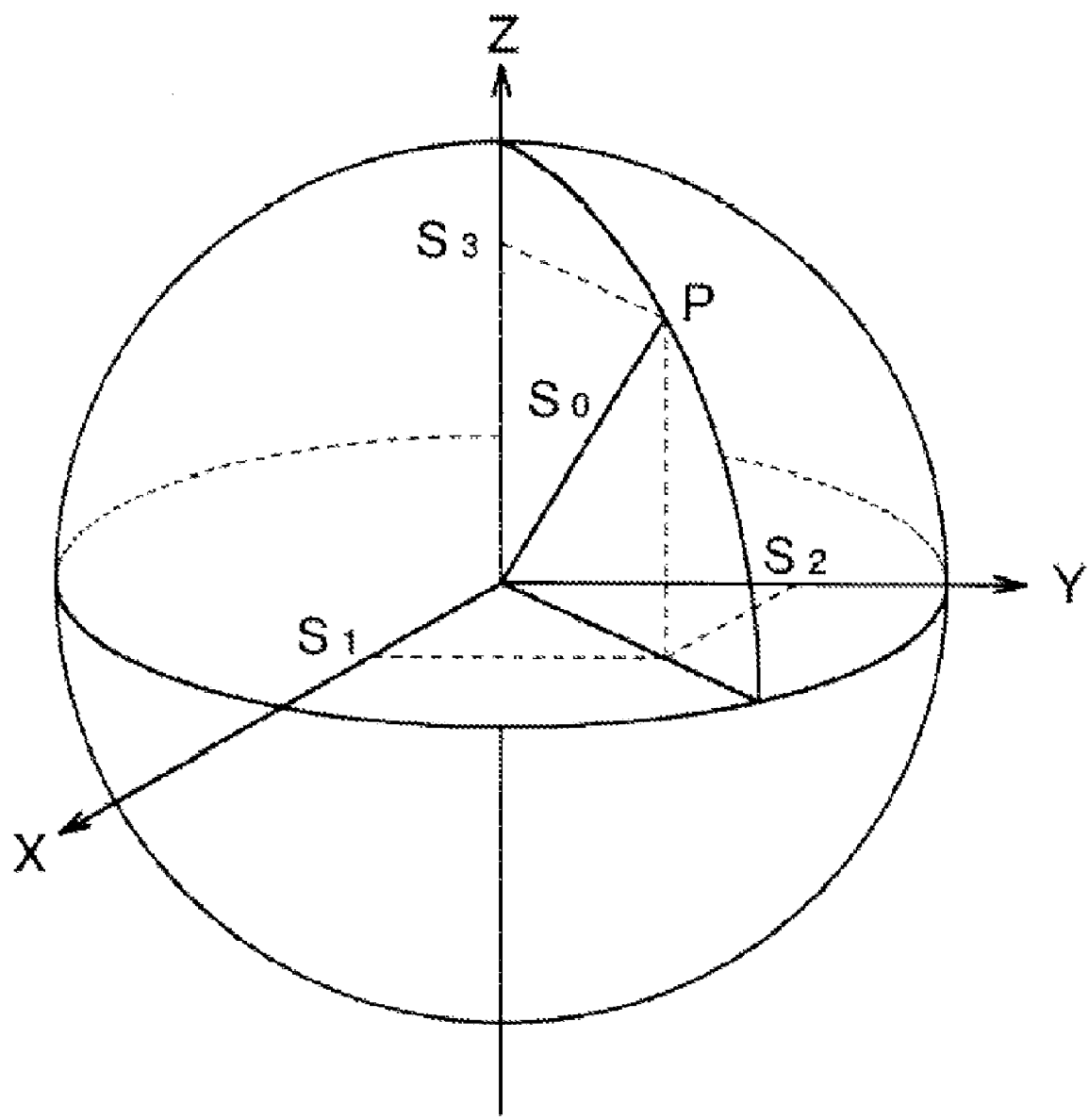
FIG. 1 illustrates a Poincare sphere showing $S_0$, $S_1$, $S_2$ and $S_3$.

Wave plates have a pair of orthogonal axes which are designated fast and slow. Polarized radiation with its electric field vector parallel to the fast axis travels faster than radiation polarized parallel to the slow axis. It has been recently shown that paper and board acts as a waveplate with its fast axis perpendicular to the fiber orientation and its slow axis parallel to the fiber orientation [See M. Reid, R. Fedosejevs, "Terahertz birefringence and attenuation properties of wood and paper", Applied Optics, pp. 2766-2772, Vol. 45, No. 12, April 2006]. The retardation of the paper waveplate is determined by the thickness of the waveplate and the fast and slow refractive indices.

The present invention is based on characterizing the Stokes parameters of electromagnetic radiation after transmission through a sheet of material, such as a paper sheet. Stokes parameters are four (4) parameters which represent a state of polarization. When measuring Stokes parameters, incident signal is typically split into four rays using a splitter such as a beam splitter, half-mirror, or filter. Each of the signal rays is given a different polarization and phase using a half-wave plate or other polarizer and a quarter-wave plate or other phase shifter, the optical components of each of the split signal rays are subjected to photoelectric conversion using photodetector elements, and computing operations are performed on the electrical signal components obtained by photoelectric conversion to obtain the Stokes parameters. Splitting of the radiation into four rays and near-simultaneous measurement of these rays under different perturbation elements (i.e. polarizer, quarter-wave plate, phase shifter) allows for essentially instantaneous measurement of the polarization state.

As known in the art, polarized radiation can be completely described by reference to the Stokes polarization parameters, or collectively as the Stokes vector. The first parameter, I, is a representation of the total intensity of the complete optical field (both polarized and unpolarized radiation). The remaining three parameters describe the polarization state of the complete optical field, i.e. in terms of linear and circular polarized radiation. As known in the art, the intensity or amplitude of unpolarized radiation remains unchanged when a polarizer is rotated, or when a retarder of some retardance value (such as that caused by paper) is introduced into the optical field, and the four (4) Stokes parameters can be applied to unpolarized radiation, partially polarized radiation and completely polarized radiation.

The present Inventors have discovered that by characterization of the Stokes parameters the fiber orientation in a fibrous sheet, such as a paper sheet, can be determined. For the transmission measurement used the radiation needs to be substantially transmitted by the sheet material, such as paper. In the case of paper, the radiation is generally from the THz regime to the microwave. Terahertz radiation, also known as terahertz waves, or terahertz radiation, generally refers to the region of the electromagnetic spectrum between 300 gigahertz ($3 \times 10^{11}$ Hz) and 3 terahertz ($3 \times 10^{12}$ Hz), corresponding to the sub millimeter wavelength range between 1 millimeter (high-frequency edge of the microwave band) and 100 micrometers (long-wavelength edge of far-infrared radiation). Microwaves are electromagnetic waves with wavelengths longer than those of terahertz (THz) frequencies, but relatively short for radio waves. Microwaves have wavelengths approximately in the range of 30 cm (frequency=1 GHz) to 1 mm (300 GHz=$3 \times 10^{11}$ Hz). Infrared radiation may also be used. Any polarimeter can generally be used for the analysis.

Polarimetry is the measurement of the polarization of radiation. A polarimeter is the scientific instrument used to make these measurements. A polarimeter can measure the complete polarization state, or the change in polarization of an unknown input beam. Polarimetry can be used to measure various optical properties of a material, including linear birefringence, circular birefringence (also known as optical rotation or optical rotary dispersion), linear dichroism, circular dichroism and scattering. To measure these various properties, there have been many designs of polarimeters, all of which can generally be used with the embodiments of the present invention. Some are archaic and some are in current use. The most sensitive polarimeters are based on interferometers, while more conventional polarimeters are based on arrangements of polarizing filters, wave plates or other devices.

The Poincare sphere representation provides a quick and easy way to understand visualization of the complete state of polarization based on the four (normalized) Stokes parameters $S_0$, $S_1$, $S_2$ and $S_3$. FIG. 1 illustrates a Poincare sphere showing $S_0$, $S_1$, $S_2$ and $S_3$. Changes in the polarized part of the signal cause the polarization state to move on the surface of the Poincare sphere.

The Stokes parameters of the output from a polarimeter are often expressed in matrix form:

$$S = \begin{pmatrix} S_0 \\ S_1 \\ S_2 \\ S_3 \end{pmatrix} \quad (1)$$

4×4 matrices representing a perturbation element to the input polarization state (also known as Mueller matrices) are multiplied against the 4×1 matrix such that $$\begin{pmatrix} S'_0 \\ S'_1 \\ S'_2 \\ S'_3 \end{pmatrix} = \begin{pmatrix} M_1 & M_2 & M_3 & M_4 \\ M_5 & M_6 & M_7 & M_8 \\ M_9 & M_{10} & M_{11} & M_{12} \\ M_{13} & M_{14} & M_{15} & M_{16} \end{pmatrix} \begin{pmatrix} S_0 \\ S_1 \\ S_2 \\ S_3 \end{pmatrix}$$

As noted above, one method for measuring Stokes parameters splits the beam into four rays that each undergo a perturbation, such as using a combination of static (i.e. non-rotating) quarter wave plate and linear polarize. In a similar method, the beam may not be split but rather the quarter wave plate and polarizer are oriented in different ways to achieve the same result. This method can be found in most textbooks on the subject and can be applied in the context of embodiments of the present invention for measuring the fiber orientation of sheet material, such as paper.

Figure 2:
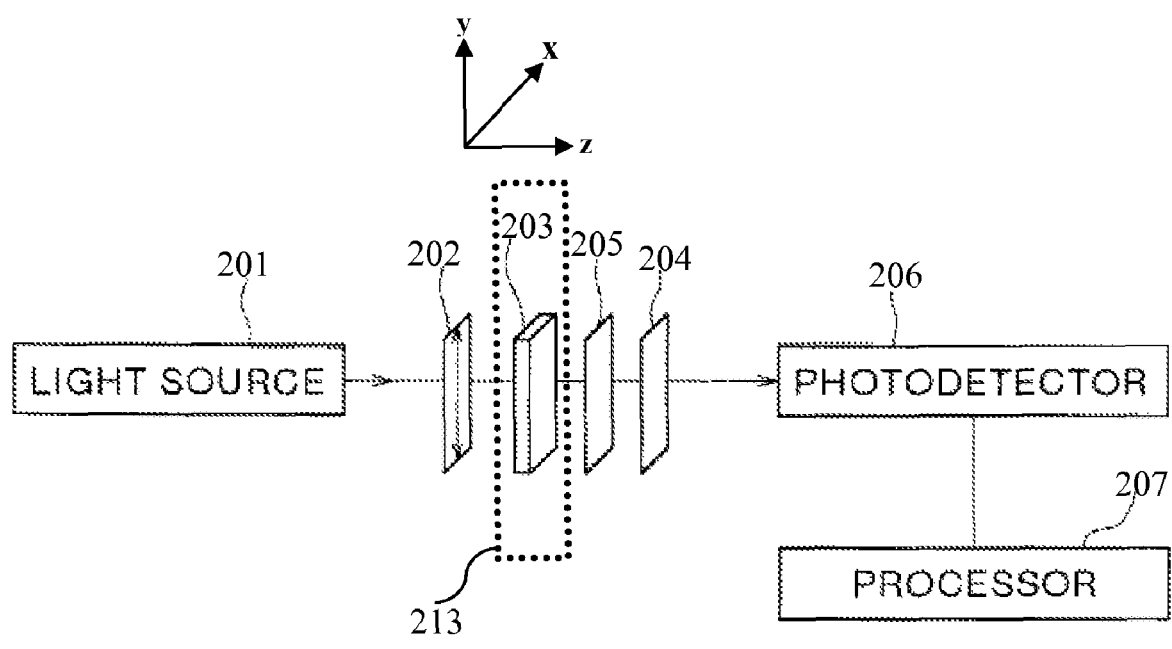
FIG. 2 is a block diagram schematically illustrating an exemplary paper fiber orientation measuring apparatus according to an embodiment of the invention.

FIG. 2 is a block diagram schematically illustrating a paper fiber orientation measuring apparatus 200 according to an embodiment of the invention. Paper web is shown as 203, which is being processed by paper production system 213, and in a typical application is in linear motion while apparatus 200 is operating. In one embodiment, an EXPRESS MOISTURE™ scanning platform (manufactured by Honeywell International) can be used in a similar location on the paper machine to current machines (e.g. after the headbox and wire). A radiation source 201, such as a pulsed THz source generated using a pulse femtosecond laser source and a photoconductive antennae or a non-linear rectification crystals such as ZnTe can provide radiation in the frequency range of 0.1 THz to 3 THz, serves as projector means, is provided to face one surface of paper web 203 of which the fiber orientation is to be determined so that the paper web 203 may be irradiated with a THz beam emitted from the antennae source 201. An alternative to the pulse THz source would be a continuous wave THz or microwave source generated from a backward wave oscillator, for example. The beam emitted from the radiation source 201 may be unpolarized, partially polarized or polarized. A beam from THz source 201 is shown aligned along a Z axis of paper web 203. The Z axis is orthogonal to both the X and Y axes as shown in FIG. 2.

Although not shown, a modulator can be added to modulate the THz beam, such as when noise is desired to be limited. In this embodiment, the detection circuitry described below generally includes a lock-in amplifier.

A polarizing plate (polarizer) 202 is shown disposed between beam source 201 and paper web 203 and in one embodiment outputs linearly polarized radiation, such as polarized parallel to the Y axis. Polarizing plate (analyzer) 204 and quarter wavelength plate 205 are shown disposed between paper web 203 and detector 206 and used in combination to determine the Stoke's parameters. Polarizing plate 204 is provided to polarize radiation transmitted by paper web 203 into three (3) different orientations in order to determine Stokes parameters $S_0$, $S_1$, and $S_2$. In embodiments of the invention these three (3) orientations can be (1) parallel to the X axis direction, (2) parallel to the Y axis direction, and (3) in a direction that is 45 degrees between the X and Y axes. Quarter wavelength plate 205 can be inserted in apparatus 200 in an axial direction that is 45 degrees from the polarizing direction of polarizing plate 204 in order to determine Stokes parameter $S_3$. Quarter wavelength plate 205 can be inserted in between paper web 203 and polarizing plate 204 or removed from the apparatus of FIG. 1 depending upon which measurements and method of measurement is to be taken.

Detector 206 measures the intensity of radiation that is transmitted through polarizing plate 202, paper web 203, polarizing plate 204, and quarter wavelength plate 205 (if present), and generates a transmitted electrical intensity signal. Detector 206 may be, for example, a synchronously gated THz antennae, a non-linear rectification crystal in combination with photodiodes, pyroelectric detector or other thermal detector. If electromagnetic radiation in a part of the EM spectrum other than in the THz (e.g. infrared or microwave) is used then detectors and sources appropriate for their generation and detection would be used. The electrical signal is generally subjected to various processing such as filtering and A/D conversion and then output to an image/data processor 207.

In mathematical form, the Stoke's parameters are determined by measuring the intensity of radiation at the photodetector 206 under different orientations of polarizer 204 and quarter-wave plate 205. Let θ be the angle of the linear polarizer 204 relative to the X-axis. Let φ be the degree of retardation of the quarter-wave plate 205. A particular intensity measurement can be represented as I(θ,φ) such that:

$S_0 = I(0°,0°) + I(90°,0°)$ No ¼ wave plate 205

$S_1 = I(0°,0°) - I(90°,0°)$ No ¼ wave plate 205

$S_2 = 2I(45°,0°) - S_0$ No ¼ wave plate 205

$S_3 = 2I(45°,90°) - S_0$ ¼ wave plate 205 inserted (90°=λ/4)

Image/data processor 207 performs predetermined processing using stored firmware to carry out a series of calculations. Specifically, image/data processor 207 computes the Stokes parameters of the paper web 203 based the transmitted radiation intensity signals reaching photodetector 206, which are used to calculate fiber orientation parameters of the paper web 203. The data calculated in this manner can be displayed on a display device such as CRT display in the form of graphs or numeric data. If desired, the data may be written into an external memory device or output from a printer. Processor 207 may be, for example, a personal computer and may include source code for calculating the Stokes parameters based upon the measured radiation intensities.

Figure 3A:
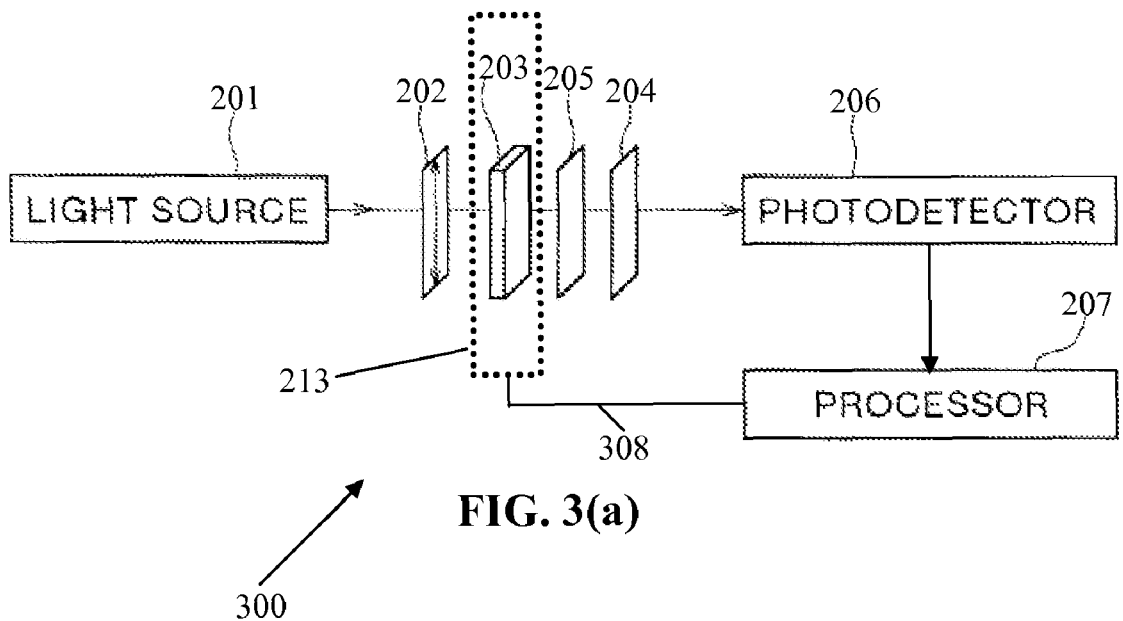
FIG. 3(a) is a block diagram schematically illustrating another exemplary paper fiber orientation measuring apparatus according to an embodiment of the invention which is analogous to the apparatus shown in FIG. 2, but adds closed loop control comprising a feedback connector which communicably connects the processor with the production system.

FIG. 3(a) is a block diagram schematically illustrating the paper fiber orientation measuring apparatus 300 according to an embodiment of the invention which is analogous to apparatus 200 shown in FIG. 2, but adds closed loop control comprising feedback connector 308 which communicably connects processor 207 with the production system 213 which is processing paper web 203. In this mode, the processor 207 acts as a process controller. Closed loop control provides for automatically modifying at least one parameter of the paper production process based on the Stokes parameters or the fiber orientation parameter(s) obtained therefrom. For example, the controlled parameter can be the jet to wire ratio (rush/drag) and/or the slice lip opening.

Figure 3B:
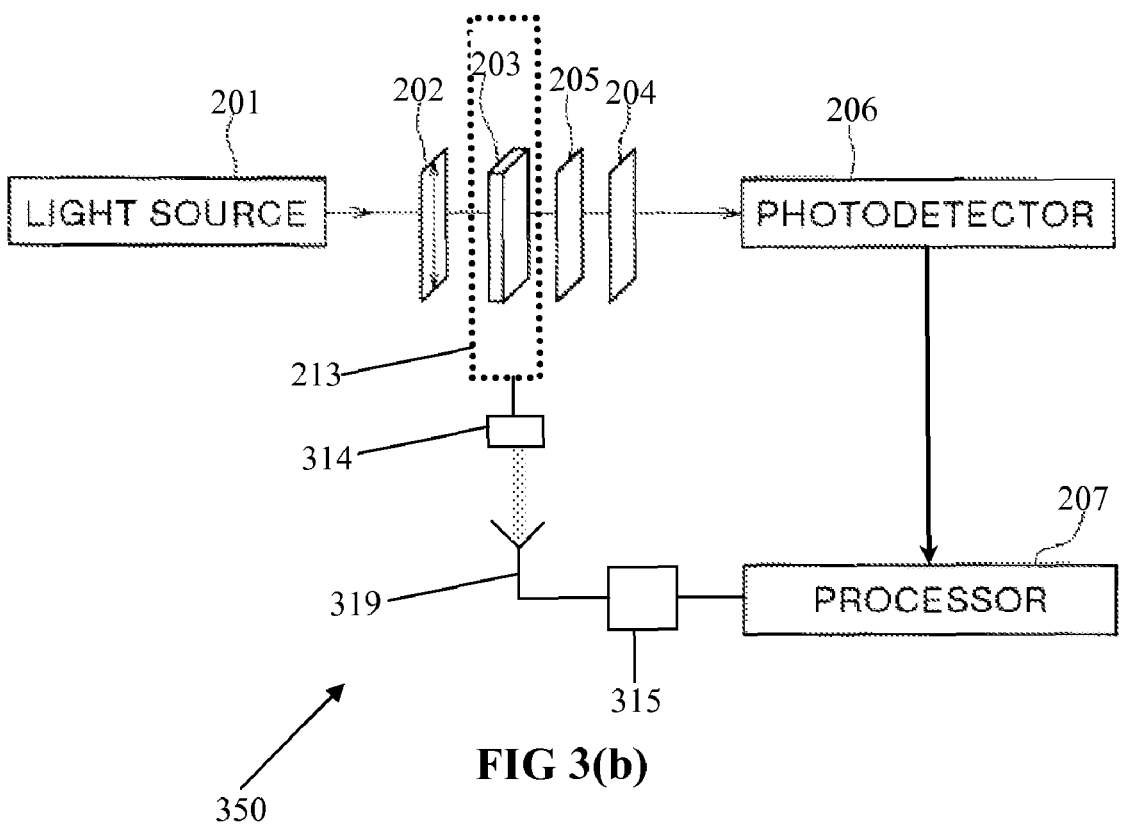
FIG. 3(b) is a block diagram schematically illustrating another exemplary paper fiber orientation measuring apparatus according to an embodiment of the invention which is analogous to the apparatus shown in FIG. 3, but instead of a wired feedback connection, utilizes a wireless link comprising a transmitter, antenna and receiver.

FIG. 3(b) is a block diagram schematically illustrating the paper fiber orientation measuring apparatus 350 according to another embodiment of the invention. Apparatus 350 is analogous to apparatus 300 shown in FIG. 3(a), but instead of a hard wired feedback connection, utilizes a wireless link comprising transmitter 315, antenna 319 and receiver 314.

In one embodiment of the invention the polarimeter comprises a rotating quarter wave plate type as disclosed in L. Giudicotti, M. Brombin, "Data analysis for a rotating quarter-wave, far-infrared Stokes polarimeter", Applied Optics, pp. 2638-2648, Vol. 46, No. 14, May 2007 (hereafter Giudicotti). This polarimeter is described below relative to FIG. 4.

As disclosed in Giudicotti, a quarter wave plate is actively rotated about its axis and the radiation intensity at the detector is integrated in different mathematical forms to obtain the Stoke's parameters, which as noted above describe the complete polarization state of the radiation beam. Equation 1 can also be written as:

$$S_0 \begin{pmatrix} 1 \\ P\cos 2\chi \cos 2\psi \\ P\cos 2\chi \sin 2\psi \\ P\sin 2\chi \end{pmatrix} \quad (2)$$

Where P, ψ, and χ are the degree of polarization, the azimuth angle, and the ellipticity angle respectively. P, ψ, and χ are calculated from the four elements of S as:

$$P = \frac{\sqrt{S_1^2 + S_2^2 + S_3^2}}{S_0} \quad (3)$$

$$\psi \begin{cases} \frac{1}{2}\arctan\left(\frac{S_2}{S_1}\right) & \text{for } S_1 > 0 \text{ and } S_2 \geq 0 \\ \frac{1}{2}\arctan\left(\frac{S_2}{S_1}\right) + \pi & \text{for } S_1 > 0 \text{ and } S_2 < 0 \\ \frac{1}{2}\arctan\left(\frac{S_2}{S_1}\right) + \frac{\pi}{2} & \text{for } S_1 < 0 \\ \frac{\pi}{2} & \text{for } S_1 = 0 \text{ and } S_2 \neq 0 \end{cases} \quad (4)$$

$$\chi = \frac{1}{2}\arcsin\left(\frac{S_3}{\sqrt{S_1^2 + S_2^2 + S_3^2}}\right) \quad (5)$$

The Stokes or (P, ψ, and χ) parameters can then be used to determine parameters including the birefringence of the paper or other sheet material, and the fiber orientation parameters of the paper or other sheet material. Measurement of the S parameters with and without (i.e. during standardize or off-sheet operation) paper allows quantifying the perturbation in polarization state caused by the paper itself (which acts as a weak retarder). For example, the Mueller matrix of a retarder with retardation strength φ and angle to input polarization θ (i.e. fiber orientation angle) takes the following form, assuming no attenuation (based on Stokes analysis):

$$\begin{pmatrix} 1 & 0 & 0 & 0 \\ 0 & \cos^2 2\theta + \cos\phi\sin^2 2\theta & (1-\cos\phi)\sin 2\theta\cos 2\theta & -\sin\phi\sin 2\theta \\ 0 & (1-\cos\phi)\sin 2\theta\cos 2\theta & \sin^2 2\theta + \cos\phi\cos^2 2\theta & \sin\phi\cos 2\theta \\ 0 & \sin\phi\sin 2\theta & -\sin\phi\cos 2\theta & \cos\phi \end{pmatrix}$$

Such that:

$$\begin{pmatrix} S_0' \\ S_1' \\ S_2' \\ S_3' \end{pmatrix} = \begin{pmatrix} 1 & 0 & 0 & 0 \\ 0 & \cos^2 2\theta + \cos\phi\sin^2 2\theta & (1-\cos\phi)\sin 2\theta\cos 2\theta & -\sin\phi\sin 2\theta \\ 0 & (1-\cos\phi)\sin 2\theta\cos 2\theta & \sin^2 2\theta + \cos\phi\cos^2 2\theta & \sin\phi\cos 2\theta \\ 0 & \sin\phi\sin 2\theta & -\sin\phi\cos 2\theta & \cos\phi \end{pmatrix} \begin{pmatrix} S_0 \\ S_1 \\ S_2 \\ S_3 \end{pmatrix}$$

Thus, in one embodiment by measuring the input and output Stokes parameters using the rotating quarter wave plate method described above or other equivalent method, φ and θ can be determined. This is one way in which fiber orientation angle could be obtained. As recognized by those having ordinary skill in the art, there are likely many other different methods using the Stokes Parameters, Poincare sphere, or (P, ψ, and χ) analysis based on perturbation in polarization state to achieve equivalent results in determining fiber orientation parameters.

Figure 4:
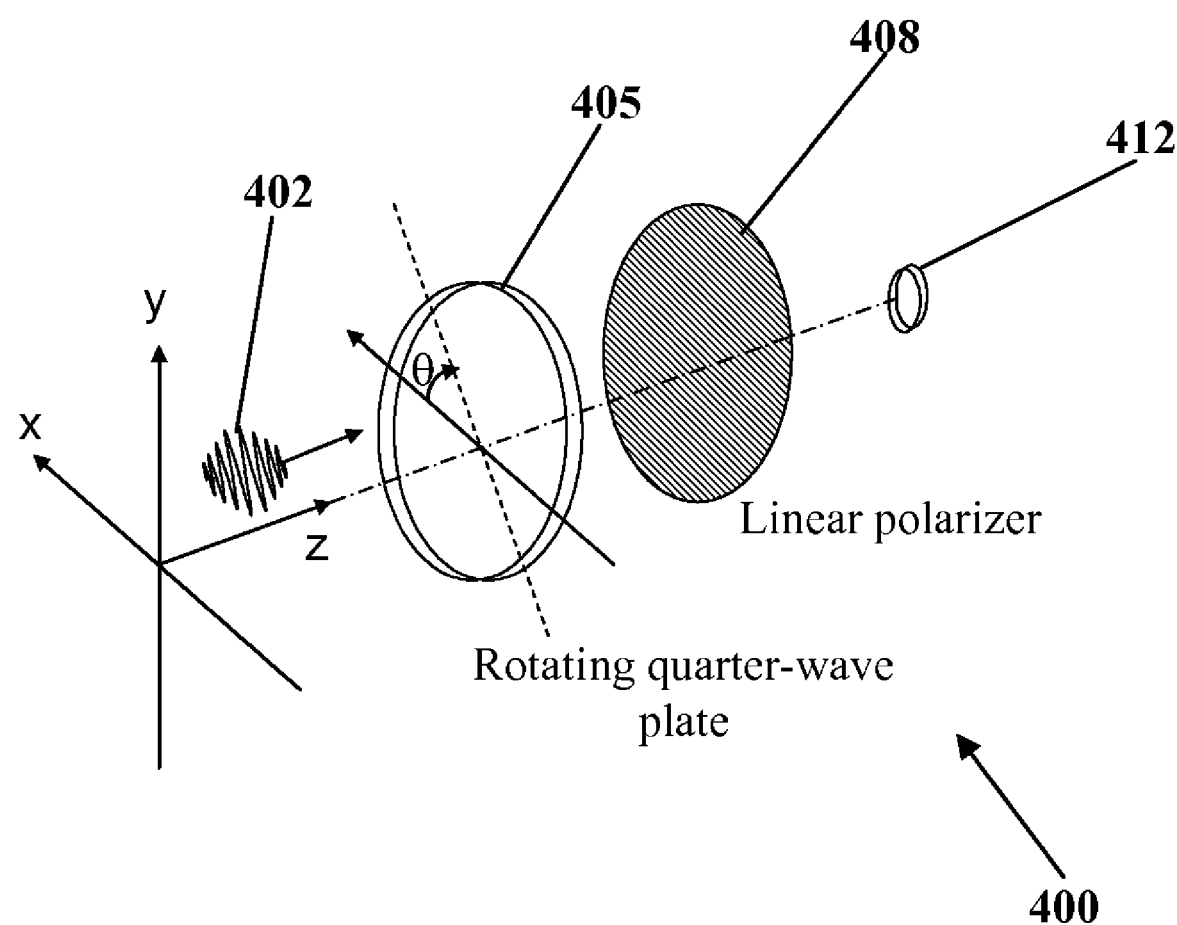
FIG. 4 shows a rotating quarter wave plate polarimeter that can be used with embodiments of the present invention comprising a rotating quarter wave plate which receives a polarized or partially polarized bean of radiation, such as a terahertz beam.

FIG. 4 shows a rotating quarter wave plate polarimeter 400 that can be used with embodiments of the present invention. Rotating quarter wave plate polarimeter 400 includes a rotating quarter wave plate 405 which receives polarized or partially polarized radiation beam 402, such as a terahertz beam.

A linear polarizer 408 follows rotating quarter wave plate 408. Detector 412, can be a synchronized THz antennae or a non-linear rectification crystal in combination with photo-diodes.

Regarding related methods for characterizing fiber orientation of paper, an exemplary method is provided. A source of polarized radiation having a frequency of at least $1\times10^8$ Hz, such as a Terahertz (far infrared) or microwave radiation source, is provided or is generated from an unpolarized source using a polarizer. The polarized radiation is transmitted through the paper.

Embodiments of the invention have been limited to a maximum frequency of 3 THz based only on limitations of the measurement setup used in a prototype system according to the invention. However, embodiments of the invention can be practiced with other measurement setups, including those available in future systems, up to a frequency beyond the upper end of the THz range, to at least about 15 THz to about 30 THz.

The method preferably derives the fiber parameters from a change in polarization (differential measurement; transformation of the polarization state). However, single measurements can be used, particularly when the input polarization state is well known. In one embodiment of the differential method, the input polarization state (in the absence of paper) is first characterized using a polarimeter and stored. A rotating quarter waveplate polarimeter, such as shown in FIG. 4, can be used to measure the polarization state of the radiation from the radiation source. In another embodiment, an achromatic quarter wave plate for the THz spectrum can be used, such as the achromatic quarter wave plate disclosed in J. Baptistse, "Terahertz achromatic quarter-wave plate", Optics Letters, Jan. 15, 2006, Vol. 31, No. 2). The radiation from the radiation source is then transmitted through the paper as it is being manufactured. The transmitted polarization state is characterized, generally using the same polarimeter. The transformation of the polarization state due to its transmission through the paper is used by a processor or other computing device to determine one or more fiber orientation parameters, such as using the relations described above.

Although described generally with respect to characterization of paper and use in paper production processes, the present invention can be broadly applied to a variety of fiber comprising sheet materials such as board, tissue, fiber glass mat or fiber reinforced composites.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A method for determining fiber orientation parameters of a sheet of material during a production process, comprising the steps of:
    irradiating a sheet of material to be characterized with polarized radiation having a frequency of at least $1\times10^8$ Hz up to 30 THz;
    measuring radiation intensities transmitted by said sheet of material;
    calculating Stokes parameters for said sheet based upon said measured radiation intensities; and
    determining at least one fiber orientation parameter from said Stokes parameters.

2. The method of claim 1, wherein said material is a moving sheet of material.

3. The method of claim 1, wherein said material comprises cellulose fibers.

4. The method of claim 3, wherein said material comprises paper being manufactured.

5. The method of claim 1, wherein said polarized radiation is generated from an unpolarized terahertz or microwave source using a polarizer, or obtained from a polarized terahertz or microwave source.

6. The method of claim 1, wherein said determining step comprises displaying said Stokes parameters on a Poincare sphere, and determining birefringence of said sheet and said fiber orientation parameter using said Poincare sphere.

7. The method of claim 1, further comprising the step of automatically modifying at least one parameter of said production process based on said Stokes parameters or said fiber orientation parameter.

8. The method of claim 1, wherein said parameter of said production process comprises at least one of jet to wire ratio (Rush/Drag) and slice lip opening.

9. The method of claim 1, wherein a polarimeter comprising a rotating quarter wave plate optically coupled to a linear polarizer is used for the measuring step.

10. The method of claim 8, further comprising the step of measuring radiation intensities of said polarized radiation without said sheet of material in a path of said polarized radiation, and using said radiation intensities of said polarized radiation without said sheet of material together with said radiation intensities transmitted by said sheet of material to quantify a perturbation in polarization state caused by said sheet of material itself.

11. The method of claim 1, wherein an angle between said sheet of material and said polarized radiation is held constant during said method.

* * * * *